United States Patent
Yi et al.

(10) Patent No.: US 7,655,786 B2
(45) Date of Patent: Feb. 2, 2010

(54) GENE EXPRESSION MODULATING ELEMENT

(75) Inventors: Hochul Yi, Cary, NC (US); Theodore M. Klein, Wilmington, DE (US); Joanne E. Barton, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 220 days.

(21) Appl. No.: 11/685,347

(22) Filed: Mar. 13, 2007

(65) Prior Publication Data

US 2008/0216201 A1 Sep. 4, 2008

Related U.S. Application Data

(60) Provisional application No. 60/782,671, filed on Mar. 15, 2006.

(51) Int. Cl.
*C07H 21/04* (2006.01)
*C12N 15/00* (2006.01)

(52) U.S. Cl. .................................... 536/24.1; 435/320.1

(58) Field of Classification Search ........................ None
See application file for complete search history.

(56) References Cited

U.S. PATENT DOCUMENTS 6,037,525 A 3/2000 Thompson et al.
6,084,155 A * 7/2000 Volrath et al. ............... 800/300

OTHER PUBLICATIONS

Bevan et al. 2000, Genbank Accession No. AL162971.*
Sequence alignment.*
Tatiana I. Gerasimova et al., Chromatin Insulators and Boundaries: Effects on Transcription and Nuclear Organization, Annu. Rev. Genet. 2001. 35:193-208.
David A Gdula et al., Genetic and Molecular analysis of the gypsy chromatin insulator of Drosophila, Proc. Natl. Acad. Sci USA, vol. 93 pp. 9378-9383, Sep. 1996.
Wei Wei et al., Polarity of transcriptional enhancement revealed by and insulator element, PNAS, vol. 97 (26) pp. 14518-14523.

* cited by examiner

*Primary Examiner*—Ashwin Mehta
*Assistant Examiner*—Li Zheng

(57) ABSTRACT

The present invention provides a method of screening for the purpose of obtaining gene expression modulating elements and gene insulator elements. The invention includes a method of identifying gene expression modulating elements and gene insulator elements through use of the following steps: a) locating intergenic regions of a plant genome that are flanked by a gene on each side that have differing gene expressions b) taking that intergenic region or a portion of that intergenic region and adding it to a cassette comprising an isolated gene c) introducing the cassette into a plant cell d) analyzing expression of the isolated gene. The present invention also includes identified sequences that act as gene expression modulating elements.

9 Claims, No Drawings

SEQUENCE LISTING

```
<160> NUMBER OF SEQ ID NOS: 4

<210> SEQ ID NO 1
<211> LENGTH: 78
<212> TYPE: DNA
<213> ORGANISM: Arabidopsis

<400> SEQUENCE: 1
acaaaattga tctctccatg tagtgttctc cacgacgaga tctggtgaca actccagttt      60
aagcaagacc aaaagact                                                    78

<210> SEQ ID NO 2
<211> LENGTH: 127
<212> TYPE: DNA
```

-continued

```
<213> ORGANISM: Arabidopsis

<400> SEQUENCE: 2
ggaccagcga gacagtttat gtgaatgttc atgcttaagt gtcgaacgta tctatctcta      60
ctatagctct gtagtcttgt tagacagtta gttttatatc tccatttttt tgtagtcttg     120
ctagttg                                                               127

<210> SEQ ID NO 3
<211> LENGTH: 114
<212> TYPE: DNA
<213> ORGANISM: Arabidopsis

<400> SEQUENCE: 3
ttgctagttg agatattacc tcttctcttc aaagtatcct tgaacgctca ccggttatga      60
aatctctaca ctatagctct gtagtcttgc tagatagtta gttctttagc tctc           114

<210> SEQ ID NO 4
<211> LENGTH: 106
<212> TYPE: DNA
<213> ORGANISM: Arabidopsis

<400> SEQUENCE: 4
attacctctt aaaagtatcc ttgaacgctt tccggttatg accaatttgt tgtagctcct      60
tgtaagtaga acttactggg accagcgaga cagtttatgt gaatgt                    106
```

US 7,655,786 B2

GENE EXPRESSION MODULATING ELEMENT

CROSS-REFERENCE TO RELATED APPLICATIONS

This application claims priority to U.S. Provisional Application Ser. No. 60/782,671 filed Mar. 15, 2006, the disclosure of which is incorporated herein by reference.

FIELD OF THE INVENTION

The invention relates to the field of plant molecular biology and biotechnology.

BACKGROUND OF THE INVENTION

Transgenic technology is widely used in biotechnology. Systems exist for transforming plant cells and regenerating complete plants from the transformed cells; structural gene and gene regulatory regions continue to be identified.

In general, the strength of a given promoter driving a transgene is a function of its inherent properties and the site of integration. Variation in transgene expression due to the site of integration is often referred to as "position effect". It would be useful to have the ability to alter the strength of a particular promoter in a predictable manner.

It is known that eukaryotic genomes have organizational properties that rely on the ability of the chromosome to establish functional elements that are not adversely affected by elements in close proximity. Polynucleotides that decrease the effects of neighboring sequences or genes are called genetic insulator elements.

SUMMARY OF THE INVENTION

The present invention provides sequences that function as gene expression modulating elements. It also provides a method to isolate sequences and screen for gene expression modulating elements.

DETAILED DESCRIPTION OF THE INVENTION

As used herein, the terms "gene expression modulating element", "modulating element", or "modulating sequence" refer to a polynucleotide that when it is combined with a polynucleotide of interest it does at least one of the following: a) stabilizes the polynucleotide of interest by decreasing or preventing the influence of other nearby DNA sequences b) increases the expression of the polynucleotide of interest or c) decreases the expression of the polynucleotide of interest. When referring to "gene expression modulating activity" the activity is the stabilization of, the increasing of, or the decreasing of the expression of the polynucleotide of interest. When referring to a stabilization in gene expression or an increase or decrease in gene expression, it is meant when compared to an appropriate control. For example, a control of a similar sequence size would be used to determine a gene expression modulating element. A stabilization in gene expression indicates a decrease in the variability of expression. Variability in expression of a gene of interest could be influenced by the position of the gene in the genome and/or by surrounding genes and gene elements such as enhancers, promoters, and terminators.

As used herein, the terms "gene insulator element", "gene insulator" or "insulator sequence" refer to a polynucleotide that, when it is combined with a polynucleotide of interest, stabilizes the polynucleotide of interest by decreasing or preventing the influence of other nearby DNA sequences. "Gene insulator activity" is the stabilizing of the expression of the polynucleotide of interest.

The term "operatively associated," as used herein, refers to DNA sequences on a single DNA molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

"Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

"Intergenic region" or "intergenic sequence" is a group of nucleotides that lie in tandem and is in between two coding regions. The intergenic region is not translated.

A "cassette" is a group of nucleotide sequences that lie in tandem. A cassette is usually integrated or exchanged as a unit. For example, a DNA cassette can be the DNA that is used in transformation. It can also be the DNA that gets integrated during recombinase-mediated integration.

"Fragments" and "variants" of the nucleotide sequences encoding recombinases and fragments and variant of recombinase proteins can also be used in the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence implements a recombination event. By "variants" is intended substantially similar sequences. For nucleotide sequences, conservative variants include those sequences that, because of the degeneracy of the genetic code, encode an amino acid sequence that retains the biological activity of a recombinase polypeptide.

The following terms are used to describe the sequence relationships between two or more polynucleotides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

As used herein "promoter" is a region of DNA to which an RNA molecule polymerase and other proteins bind to initiate transcription.

A "marker gene" is a sequence of DNA that when expressed allows it to be identified. A marker may be a selectable marker gene, a polynucleotide of interest or any gene that produces an identifiable product. The product is either screenable, scorable, visible or detectable. Any gene that produces a protein that can be detected through an ELISA may be considered a marker gene. For example, reporter genes, exemplified by chloramphenicol acetyl transferase and beta-glucuronidase (GUS; see, e.g., Jefferson et al. 1987, EMBO J. 6:3901-3907), are commonly used to assess transcriptional and translational competence of chimeric constructions. Other suitable genes include GFP (green florescence protein; Chalfie et al. (1994) Science 263:802), luciferase (Riggs et al. (1987) Nucleic Acids Res. 15(19):8115; Luehrsen et al. (1992) Methods Enzymol. 216:397-414) and genes encoding for anthocyanin production (Ludwig et al. (1990) Science 247:449). Standard assays are available to sensitively detect marker gene activity in a transgenic organism.

A "transgene" is a recombinant DNA construct that has been introduced into the genome by a transformation procedure.

An "isolated" nucleic acid molecule or protein, or biologically active portion thereof, is substantially or essentially free from components that normally accompany or interact with the nucleic acid molecule or protein as found in its naturally occurring environment.

An "isolated gene" is free of sequences that naturally flank the gene (i.e., sequences located at the 5' and 3' ends of the gene) in the genomic DNA of the organism from which the gene is derived.

A "gene of interest" is any gene which, when transferred to a plant or plant cell, confers a characteristic. For example any gene that confers virus resistance, insect resistance, disease resistance, pest resistance, herbicide resistance, improved nutritional value, improved yield, change in fertility, production of a useful enzyme or metabolite in a plant could be a gene of interest.

A "polynucleotide of interest" is any polynucleotide which, when transferred to a plant or plant cell, confers a desired characteristic. For example any polynucleotide that confers virus resistance, insect resistance, disease resistance, pest resistance, herbicide resistance, improved nutritional value, improved yield, change in fertility, production of a useful enzyme or metabolite in a plant could be a polynucleotide of interest.

A "selectable marker" is any gene whose expression in a cell gives the cell a selective advantage. The selective advantage possessed by the cells with the selectable marker gene may be due to their ability to grow in the presence of a negative selective agent, such as a antibiotic or a herbicide, compared to the ability to grow cells not containing the gene. The selective advantage possessed by the cells containing the gene may also be due to their enhanced capacity to utilize an added compound such as a nutrient, growth factor or energy source.

As used herein a "sexual cross", "cross" and "sexually crossing" encompass any means by which two haploid gametes are brought together resulting in a successful fertilization event and the production of a zygote. By "gamete" is intended a specialized haploid cell, either a sperm or an egg, serving for sexual reproduction. By "zygote" is intended a diploid cell produced by fusion of a male and female gamete (i.e. a fertilized egg). The resulting "hybrid" zygote contains chromosomes from both the acceptor and donor plant. The zygote then undergoes a series of mitotic divisions to form an embryo.

As defined herein, a "genetically modified plant cell" is a cell that comprises a stably integrated DNA sequence of interest.

As defined herein, the "transgenic plant" is a plant that comprises a stably integrated DNA sequence of interest.

As used herein, "heterologous" in reference to a nucleic acid is a nucleic acid that originates from a foreign species, or, if from the same species, is substantially modified from its native form in composition and/or genomic locus by deliberate human intervention. For example, a modulating sequence or insulator sequence that may be derived from the species of the host cell and is placed in a transgene is considered a heterologous sequence due to a location change. For example, a promoter operably linked to a heterologous structural gene is from a species different from that from which the structural gene was derived, or, if from the same species, one or both are substantially modified from their original form and/or genomic location.

By "host cell" is meant a cell, which comprises a heterologous nucleic acid sequence of the invention. Host cells may be prokaryotic cells such as E. coli, or eukaryotic cells such as yeast, insect, amphibian, or mammalian cells. Optimally, host cells are monocotyledonous or dicotyledonous plant cells. A particularly optimal monocotyledonous host cell is a maize host cell.

The present invention provides a method of making a transformed plant cell said method comprising: a) providing a plant cell b) transforming said plant cell with an isolated nucleic acid wherein said isolated nucleic acid comprises a polynucleotide of interest and a gene expression modulating element and wherein said gene expression modulating element has similar sequence identity to SEQ. ID NO. 1, 2, 3, or 4. An embodiment of the invention is an isolated polynucleotide comprising SEQ. ID NO. 1, 2, 3, or 4 or a complementary sequence thereof. Another embodiment of this invention is an isolated polynucleotide comprising a sequence with 90%, 95%, 97%, 99% identity to SEQ. ID NO. 1, 2, 3, or 4 or a complementary sequence thereof. Another embodiment of the invention is an isolated polynucleotide that comprises the consensus sequence derived from SEQ. ID NO. 1, 2, 3, or 4. The isolated polynucleotide comprising the consensus sequence can be 20, 30, or 40 bp to 150 bp but is not limited to these lengths. Another embodiment of the present invention is an isolated sequence containing SEQ. ID NO. 1, 2, 3, or 4 that has gene expression modulating element or gene insulator element activity. Another embodiment of the present invention is an isolated sequence comprising a combination of portions of SEQ. ID NO. 1, 2, 3, or 4 that has gene expression modulating element or gene insulator element activity. Another embodiment is any isolated polynucleotide that comprises 20, 30, 40, 50, or 60 continuous nucleotides of SEQ. ID NO. 1, 2, 3, or 4 that has gene expression modulating element or gene insulator element activity.

```
SEQ ID 1: >14-II-2
acaaaattgatctctccatgtagtgttctccacgacgagatctggtgaca actccagtttaagcaagaccaaaagact SEQ ID 2: >5-IV-1
ggaccagcgagacagtttatgtgaatgttcatgcttaagtgtcgaacgta tctatctctactatagctctgtagtcttgttagacagttagttttatatc tccattttttgtagtcttgctagttg SEQ ID 3: >5-IV-2
ttgctagttgagatattacctcttctcttcaaagtatccttgaacgctca ccggttatgaaatctctacactatagctctgtagtcttgctagatagtta gttctttagctctc SEQ ID 4: >5-III-5
attacctcttaaaagtatccttgaacgctttccggttatgaccaatttgt tgtagctccttgtaagtagaacttactgggaccagcgagacagtttatgt gaatgt
```

The present invention provides a method of screening for the purpose of obtaining gene expression modulating elements and gene insulator elements. One embodiment is a method of identifying gene expression modulating elements and gene insulator elements said method comprising: a) locating intergenic regions of a plant genome that are flanked by a gene on each side wherein the first gene has a different expression pattern than the second gene b) taking said intergenic region or a portion of said intergenic region and adding it to a cassette comprising an isolated gene c) introducing said cassette into a plant cell d) analyzing expression of said isolated gene in said plant cell. Another embodiment of the present invention is said method wherein the intergenic regions are less than 2 kb nucleotides in length. One embodiment is said method wherein the intergenic region or a portion of said region is placed in front of the 5' region of the promoter of the isolated gene, after the promoter and before the coding region of the isolated gene, after the isolated gene, or within the promoter sequence. One embodiment is wherein said intergenic region or a portion of said intergenic region is placed between the core promoter and the enhancer region of the isolated gene. One embodiment of the present invention is the gene expression modulating elements that are derived from said method of screening.

The gene expression modulating element may be located at various positions. For example, the modulating element may be located before the promoter, within the promoter, after the promoter and before the coding region of the polynucleotide of interest or after the coding region of the polynucleotide of interest. The modulating elements can protect transgenes either from surrounding native influences or can be used to protect transgenes from interacting with each other in a multigene cassette. The modulating elements can be used to block the influence of enhancers. The modulating elements can be placed between two genes adjacent to each other for setting clear boundary between two promoters and prevent unwanted interference of gene expression. The non-coding intergenic DNA elements are useful for improving and solving current obstacles such as transcriptional interference, chromatin repression, expression variegation for high transformation efficiency and transgenic plants recovery.

Introducing in the present invention can be through transient transformation, stable transformation, and/or through DNA integration recombinase systems.

Intergenic regions of a plant genome wherein the first gene has a different expression pattern than the second gene can be located using any combination of bioinformatics tools, molecular maps, and expression data. Expression data can be obtained through various means such as Western analysis, microarray analysis, Northern blots, nuclear run on analysis, RT-PCR, quantitative real-time RT-PCR, and public databases (Pennisi, Science 286, 449 (1999); Kaiser, (ed.) Science 286, 1047 (1999)). Different expression patterns can be different at different times, throughout the development of the plant, in response to environment changes, and/or due to cell type. Different expression patterns may be consistent over time and development but may be different in amounts of expression only. The amount of product expressed by the two genes flanking the intergenic region can vary. For the two genes to be considered as having different expression patterns the amount of product difference, RNA or protein, may be 100 ppm or greater, 100 ppm to 1000 ppm, or 1000 ppm or greater at any point in time.

The length of the intergenic region in this invention can be less than, 3 kb, less than 2 kb, less than 1.75 kb, less than 1.5 kb or less than 1 kb. The length of the intergenic region can be from 20 base pairs to 2 kb, 30 base pairs to 2 kb, 20 base pairs to 1.75 kb, 30 base pairs to 1.75 kb, 20 base pairs to 3 kb, 30 base pairs to 3 $k$b, 40 base pairs to 1.5 kb, and 40 base pairs to 2 kb.

The intergenic region can be divided into portions for screening. These portions can be any length from 20 bp to about 1 kb in length.

The present invention includes gene expression modulating elements and gene insulator elements. One embodiment is gene expression modulating elements and gene insulator elements that range in length from 20 to 200 bp, from 20 to 150 bp, from 20 to 100 bp, from 30 to 200 bp, and from 40 to 200 bp.

The methods of the invention can be carried out with cells from a variety of different plant cells. The cells may be monocots or dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Embodiments of this invention include sequences that have 80%, 85%, 90%, 95%, 97%, 98%, 99% and 100% identity to SEQ. ID NO. 1, 2, 3, or 4 and isolated nucleic acids fully complementary thereof. Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877. Embodiments of this invention include fragments and combinations of fragments among the SEQ ID NO. 1, 2, 3, and 4.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) *CABIOS* 8:155-65; and Pearson et al. (1994) Meth. Mol. Biol. 24:307-331. The ALIGN program is based on the algorithm of Myers and Miller (1988) supra. When utilizing BLAST, Gapped BLAST, PSI-BLAST, the default parameters of the respective programs (e.g., BLASTN for nucleotide sequences, BLASTX for proteins) can be used. See the world wide web ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3; or any equivalent program thereof. By "equivalent program" is intended any sequence comparison program that, for any two sequences in question, generates an alignment having identical nucleotide and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

There are many genes of interest or polynucleotides of interest that can be used in transgenes and therefore can be used in this invention. Polynucleotides of interest that when expressed can confer herbicide resistance, insect resistance, disease resistance, drought tolerance, male sterility, restoration of male fertility, amino acid changes, nutritional improvements, agronomic improvements, changes in maturity, increase in yield, changes in flowering time, increases in protein, increases in starch, decreases in starch, changes in phytate content, increase in oil, change in the oil content, or increases in transformation efficiency. Exemplary polynucleotides of interest implicated in this regard include, but are not limited to, those categorized below.

1. Transgenes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (Arabidopsis RSP2 gene for resistance to *Pseudomonas syringae*). A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and hereby are incorporated by reference for this purpose: U.S. Pat. Nos. 5,188,960; 5,689,052; 5,880,275; and WO 97/40162.

(C) A lectin. See, for example, the disclosure by Van Damme et al., Plant Molec. Biol. 24:25 (1994), who disclose the nucleotide sequences of several *Clivia miniata* mannose-binding lectin genes.

(D) A vitamin-binding protein such as avidin. See PCT application U.S.93/06487 the contents of which are hereby incorporated by reference for this purpose. The application teaches the use of avidin and avidin homologues as larvicides against insect pests.

(E) An enzyme inhibitor, for example, a protease inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), and Sumitani et al., Biosci. Biotech. Biochem. 57:1243 (1993) (nucleotide sequence of *Streptomyces nitrosporeus* α-amylase inhibitor) and U.S. Pat. No. 5,494,813.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

(G) A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

(H) A hydrophobic moment peptide. See PCT Application WO95/16776 (disclosure of peptide derivatives of Tachyplesin which inhibit fungal plant pathogens) and PCT Application WO95/18855 (teaches synthetic antimicrobial peptides that confer disease resistance), the respective contents of which are hereby incorporated by reference for this purpose.

(I) A membrane permease, a channel former or a channel blocker. For example, see the disclosure by Jaynes et al., Plant Sci. 89:43 (1993), of heterologous expression of a cecropin-β lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-induced resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

(K) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

(L) A developmental-arrestive protein produced in nature by a plant. For example, Logemann et al., Bio/Technology 10:305 (1992), have shown that transgenic plants expressing the barley ribosome-inactivating gene have an increased resistance to fungal disease.

(M) Genes involved in the Systemic Acquired Resistance (SAR) Response and/or the pathogenesis related genes. Briggs, S., Current Biology 5:128-131 (1995).

(N) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998).

2. Transgenes that Confer Resistance to an Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate which has resistance imparted by mutant 5-enolpyrvl-3-phosphikimate synthase (EPSP) and aroA genes, respectively. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 F; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463, 175, which are incorporated herein by reference for this purpose. In addition glyphosate resistance can be imparted to plants by the over expression of genes encoding glyphosate N-acetyltransferase (GAT). See, for example, PCT publication WO02/36782 and U.S. application Ser. No. 10/427,692 which has published as US 2004/0082770. A DNA molecule encoding a mutant aroA gene can be obtained under ATCC Accession No. 39256, and the nucleotide sequence of the mutant gene is disclosed in U.S. Pat. No. 4,769,061 to Comai.

(C) Phosphono compounds such as glufosinate (phosphinothricin acetyl transferase (PAT) and *Streptomyces hygroscopicus* phosphinothricin acetyl transferase (bar) genes. The nucleotide sequence of a phosphinothricin-acetyl-transferase gene is provided in European Patent No. 0 242 246 and 0 242 236 to Leemans et al., De Greef et al., Bio/Technology 7:61 (1989), describe the production of transgenic plants that express chimeric bargenes coding for phosphinothricin acetyl transferase activity. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose.

(D) Pyridinoxy or phenoxy proprionic acids and cycloshexones (ACCase inhibitor-encoding genes). Exemplary of genes conferring resistance to phenoxy proprionic acids and cycloshexones, such as sethoxydim and haloxyfop, are the Acc1-S1, Acc1-S2 and Acc1-S3 genes described by Marshall et al., Theor. Appl. Genet. 83:435 (1992).

(E) A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

(F) Acetohydroxy acid synthase, which has been found to make plants that express this enzyme resistant to multiple types of herbicides, has been introduced into a variety of plants (see, e.g., Hattori et al. (1995) Mol Gen Genet 246: 419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(G) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and International Publication WO 01/12825, which are incorporated herein by reference for this purpose.

3. Transgenes that Confer or Contribute to a Grain Trait, such as:

(A) Modified fatty acid metabolism, for example, by transforming a plant with a gene that suppresses stearoyl-ACP desaturase to increase stearic acid content of the plant. See Knultzon et al., Proc. Natl. Acad. Sci. USA 89:2624 (1992).

(B) Phytate Content
(1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene.
(2) A gene could be introduced that reduces phytate content. Examples of genes are disclosed in U.S. Pat. Nos. 6,197,561; 6,291,224 and WO 02/059324.

(C) Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus mutans* fructosyltransferase gene), Steinmetz et al., Mol. Gen. Genet. 200:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., Plant Physiol. 102:1045 (1993) (maize endosperm starch branching enzyme II). U.S. Pat. Nos. 6,43,886 and 6,399,859 disclose starch synthase genes in maize.

(D) Elevated oleic acid via FAD-2 gene modification and/or decreased linolenic acid via FAD-3 gene modification (see U.S. Pat. Nos. 6,063,947; 6,323,392; and WO 93/11245).

4. Genes that Control Male-Sterility:

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al., Plant Mol. Biol. 19:611-622, 1992).

A number of promoters can be used in the practice of the invention. The promoters can be selected based on the desired outcome. That is, the nucleic acid can be combined with constitutive, tissue-preferred, developmentally regulated, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. The Cauliflower Mosaic Virus 35S promoter is one of the promoters used most often for dicot transformation because it confers high levels of gene expression in almost all tissues (J. Odell et al., 1985; D. W. Ow et al., 1986; D. M. Shah et al., 1986). Modifications of this promoter are also used, including a configuration with two tandem 35S promoters (R. Kay et al., 1987) and the mas-35S promoter (L. Comai et al., 1990), which consists of the mannopine synthase promoter in tandem with the 35S promoter. Both of these promoters drive even higher levels of gene expression than a single copy of the 35S promoter. Other viral promoters that have been used include the Cauliflower Mosaic Virus 19S promoter (J. Paszkowski et al., 1984; E. Balazs et al.) and the 34S promoter from the figwort mosaic virus (M. Sanger et al., 1990).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced ODP2 expression within a particular plant tissue.

Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2):157-168; Rinehart et al. (1996) Plant Physiol. 112(3): 1331-1341; Van Camp et al. (1996) Plant Physiol. 112(2): 525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); and, milps (myo-inositol-1-phosphate synthase); (see WO 00/11177 and U.S. Pat. No. 6,225,529; herein incorporated by reference). Gamma-zein is another endosperm-specific promoter (Boronat et al. (1986) Plant Science 47:95-102). Globulin-1 (Glob-1) is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference. Additional seed-preferred promoters include the oleosin promoter (WO 00/0028058), the lipid transfer protein (LTP) promoter (U.S. Pat. No. 5,525,716). Additional seed-preferred promoters include the Lec1 promoter, the Jip1 promoter, and the milps3 promoter (see, WO 02/42424). Lec1-indicates a leafy cotyledon 1 transcriptional activator polynucleotide. See U.S. patent application Ser. No. 09/435, 054 which is U.S. Pat. No. 6,825,397. Lec1 promoter is characterized in U.S. Pat. No. 7,122,658.

Both heterologous and non-heterologous (i.e., endogenous) promoters can be employed to direct expression of the polynucleotide of interest and therefore influenced by modulating elements and insulating elements.

The methods of the invention involve introducing a nucleotide construct or a polypeptide into a plant. By "introducing" is intended presenting to the plant the nucleotide construct (i.e., DNA or RNA) or a polypeptide in such a manner that the nucleic acid or the polypeptide gains access to the interior of a cell of the plant. The methods of the invention do not depend on a particular method for introducing the nucleotide construct or the polypeptide to a plant, only that the nucleotide construct gains access to the interior of at least one cell of the plant. Methods for introducing nucleotide constructs and/or polypeptides into plants are known in the art including, but not limited to, stable transformation methods, transient transformation methods, virus-mediated methods, DNA integration recombinase systems.

By "stable transformation" is intended that the nucleotide construct introduced into a plant integrates into the genome of the plant and is capable of being inherited by progeny thereof. By "transient transformation" is intended that a nucleotide construct or the polypeptide introduced into a plant does not integrate into the genome of the plant.

In preparing a DNA cassette, various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The DNA cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (*Virology* 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods or sequences known to enhance translation can also be utilized, for example, introns, and the like.

The method of transformation is not critical to the invention; various methods of transformation are currently available. As newer methods are available to transform host cells they may be directly applied. Accordingly, a wide variety of methods have been developed to insert a DNA sequence into the genome of a host cell to obtain the transcription and/or translation of the sequence. Thus, any method that provides for efficient transformation/transfection may be employed.

Methods for transforming various host cells are disclosed in Klein et al. "Transformation of microbes, plants and animals by particle bombardment", Bio/Technol. New York, N.Y., Nature Publishing Company, March 1992, 10(3):286-291. Techniques for transforming a wide variety of higher plant species are well known and described in the technical, scientific, and patent literature. See, for example, Weising et al., Ann. Rev. Genet. 22:421-477 (1988).

For example, the DNA construct may be introduced directly into the genomic DNA of the plant cell using techniques such as electroporation, PEG-induced transfection, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in Plant Cell, Tissue and Organ Culture, Fundamental Methods. eds. O. L. Gamborg and G. C. Phillips. Springer-Verlag Berlin Heidelberg N.Y., 1995. The introduction of DNA constructs using polyethylene glycol precipitation is described in Paszkowski et al., Embo J. 3:2717-2722 (1984). Electroporation techniques are described in Fromm et al., Proc. Natl. Acad. Sci. 82:5824 (1985). Ballistic transformation techniques are described in Klein et al., Nature 327:70-73 (1987).

Alternatively, the DNA constructs may be combined with suitable T-DNA flanking regions and introduced into a *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques are well described in the scientific literature. See, for example Horsch et al., Science 233:496-498 (1984), and Fraley et al., Proc. Natl. Acad. Sci. 80:4803 (1983). For instance, *Agrobacterium* transformation of maize is described in U.S. Pat. No. 5,981, 840. *Agrobacterium* transformation of monocot is found in U.S. Pat. No. 5,591,616. *Agrobacterium* transformation of soybeans is described in U.S. Pat. No. 5,563,055.

Other methods of transformation include (1) *Agrobacterium rhizogenes*-induced transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-induced DNA uptake (see, e.g., Freeman et al., Plant Cell Physiol. 25:1353, 1984), (3) the vortexing method (see, e.g., Kindle, Proc. Natl. Acad. Sci., USA 87:1228, (1990).

DNA can also be introduced into plants by direct DNA transfer into pollen as described by Zhou et al., Methods in Enzymology 101:433 (1983); D. Hess, Intern Rev. Cytol. 107:367 (1987); Luo et al., Plant Mol. Biol. Reporter, 6:165 (1988). Expression of polypeptide coding nucleic acids can be obtained by injection of the DNA into reproductive organs of a plant as described by Pena et al., Nature 325:274 (1987). Transformation can also be achieved through electroporation of foreign DNA into sperm cells then microinjecting the transformed sperm cells into isolated embryo sacs as described in U.S. Pat. No. 6,300,543 by Cass et al. DNA can also be injected directly into the cells of immature embryos and the rehydration of desiccated embryos as described by Neuhaus et al., Theor. Appl. Genet. 75:30 (1987); and Benbrook et al., in Proceedings Bio Expo 1986, Butterworth, Stoneham, Mass., pp. 27-54 (1986).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., The Plant Cell 2:603-618 (1990).

Introducing a polynucleotide sequence into a cell can be achieved using a DNA integration recombinase system. DNA integration recombinase systems involve DNA cassettes one, which can be identified as "donor DNA" and one, which can be identified as "target DNA". The target DNA generally comprises at least two recombinase recognition sites. The sites flank a polynucleotide that may comprise a gene or a set of gene expression cassettes. In the present invention the recombination recognition sites can be identical and/or non-identical. The donor DNA generally comprises at least two recombinase recognition sites. The sites flank a polynucleotide that may comprise a gene or a set of gene expression cassettes. DNA integration recombinase systems also have one or more proteins, called recombinases, which mediate the specific cleavage and ligation of the recombinase recognition sites. The recombinases can enter the system in various ways. For instance, a polynucleotide encoding the recombinase could be within the target DNA, the donor DNA, within the genome of a target plant, or within the genome of the donor plant. The recombinase could also enter the system via transient expression or as an active recombinase. The donor DNA can be initially integrated into the plant cell through transformation. After the donor DNA has been stably integrated into the plant cell, more genetically modified cells can be propagated from the transformed plant cell or plants can be obtained from the transformed plant cells and the donor DNA can be inherited via sexual and asexual reproduction. The target DNA can also be initially integrated into the plant cell through transformation. After the target DNA is stably integrated into the plant cell more genetically modified cells can be propagated from the transformed plant cell or plants can be obtained from the transformed plant then cells and the target DNA can be inherited via sexual and asexual reproduction.

After the donor DNA and the target DNA have been stably integrated into separate plants, creating a donor plant and a target plant, the plants then can be sexually crossed. Recombinase-mediated integration can occur with the crossing of the donor plant and the target plant in the presence of corresponding recombinase. The term "crossing" does not designate which plant is to be used as a male and which plant is to be used as a female, thus for purposes of this invention the plant containing the target DNA can be used as either the male or female in the cross.

The donor DNA and the target DNA can also be brought together through transformation of cells. If the donor DNA is stably integrated into a cell, the target DNA can then be used to transform the cell. In the presence of corresponding recombinase, recombinase-mediated integration can occur. If the target DNA is stably integrated into a cell, the donor DNA then can be used to transform the cell. Once again in the presence of corresponding recombinase, recombinase-mediated integration can occur.

Examples of recombination sites for use in the invention are known in the art and include FRT sites (See, for example, U.S. Pat. No. 6,187,994; Schlake and Bode (1994) Biochemistry 33:12746-12751; Huang et al. (1991) Nucleic Acids Research 19:443-448; Paul D. Sadowski (1995) In Progress in Nucleic Acid Research and Molecular Biology 51:53-91; Michael M. Cox (1989) *In Mobile DNA*, Berg and Howe (eds) American Society of Microbiology, Washington D.C., pp. 116-670; Dixon et al. (1995) 18:449-458; Umlauf and Cox (1988) The EMBO Journal 7:1845-1852; Buchholz et al. (1996) Nucleic Acids Research 24:3118-3119; Kilby et al. (1993) Trends Genet. 9:413-421; Rossant and Geagy (1995) Nat. Med. 1:592-594; Albert et al. (1995) The Plant J. 7:649-659; Bayley et al. (1992) Plant Mol. Biol. 18:353-361; Odell et al. (1990) Mol. Gen. Genet. 223:369-378; and Dale and Ow (1991) Proc. Natl. Acad. Sci. USA 88:10558-105620; all of which are herein incorporated by reference); lox (Albert et al. (1995) Plant J. 7:649-659; Qui et al. (1994) Proc. Natl. Acad. Sci. USA 91:1706-1710; Stuurman et al. (1996) Plant Mol. Biol. 32:901-913; Odell et al. (1990) Mol. Gen. Gevet. 223: 369-378; Dale et al. (1990) Gene 91:79-85; and Bayley et al. (1992) Plant Mol. Biol. 18:353-361.) Dissimilar recombination sites are designed such that integrative recombination events are favored over the excision reaction. Such dissimilar recombination sites are known in the art. For example, Albert et al. introduced nucleotide changes into the left 13 bp element (LE mutant lox site) or the right 13 bp element (RE mutant lox site) of the lox site. Recombination between the LE mutant lox site and the RE mutant lox site produces the wild-type loxP site and a LE+RE mutant site that is poorly recognized by the recombinase Cre, resulting in a stable integration event (Albert et al. (1995) Plant J. 7:649-659). See also, for example, Araki et al. (1997) Nucleic Acid Research 25:868-872.

Various recombinases can be used in this invention. For reviews of site-specific recombinases, see Sauer (1994) Current Opinion in Biotechnology 5:521-527; and Sadowski (1993) FASEB 7:760-767; the contents of which are incorporated herein by reference. The recombinase used in the methods of the invention can be a naturally occurring recombinase or an active fragment or variant of the recombinase. Recombinases useful in the methods and compositions of the invention include recombinases from the Integrase and Resolvase families, biologically active variants and fragments thereof, and any other naturally occurring or recombinantly produced enzyme or variant thereof, that catalyzes conservative site-specific recombination between specified DNA recombination sites. The Integrase family of recombinases has over one hundred members and includes, for example, FLP, Cre, Int and R. For other members of the Integrase family, see for example, Esposito et al. (1997) Nucleic Acid Research 25:3605-3614 and Abremski et al. (1992) Protein Engineering 5:87-91, both of which are herein incorporated by reference. Such recombination systems include, for example, the streptomycete bacteriophage phi C31 (Kuhstoss et al. (1991) J. Mol. Biol. 20:897-908); the SSV1 site-specific recombination system from *Sulfolobus shibatae* (Maskhelishvili et al. (1993) Mol. Gen. Genet. 237: 334-342); and a retroviral integrase-based integration system (Tanaka et al. (1998) Gene 17:67-76). In other embodiments, the recombinase is one that does not require cofactors or a supercoiled substrate. Such recombinases include Cre, FLP, or active variants or fragments thereof. See U.S. Pat. No. 5,929,301.

The FLP recombinase is a protein that catalyzes a site-specific reaction that is involved in amplifying the copy number of the two-micron plasmid of *S. cerevisiae* during DNA replication. The FLP recombinase catalyzes site-specific recombination between two FRT sites. The FLP protein has been cloned and expressed. See, for example, Cox (1993) Proc. Natl. Acad. Sci. USA 80:4223-4227. The FLP recombinase for use in the invention may be that derived from the genus *Saccharomyces*. One can also synthesize the recombinase using plant-preferred codons for optimal expression in a plant of interest. A recombinant FLP enzyme encoding by a nucleotide sequence comprising maize preferred codons (moFLP) that catalyzes site-specific recombination events is known. See, for example, U.S. Pat. No. 5,929,301, herein incorporated by reference. Additional functional variants and fragments of FLP are known. See, for example, Hartung et al. (1998) J. Biol. Chem. 273:22884-22891 and Saxena et al. (1997) Biochim Biophys Acta 1340(2):187-204, and Hartley et al. (1980) Nature 286:860-864, all of which are herein incorporated by reference.

The bacteriophage recombinase Cre catalyzes site-specific recombination between two lox sites. The Cre recombinase is known in the art. See, for example, Guo et al. (1997) Nature 389:40-46; Abremski et al. (1984) J. Biol. Chem. 259:1509-1514; Chen et al. (1996) Somat. Cell Mol. Genet. 22:477-488; and Shaikh et al. (1977) J. Biol. Chem. 272:5695-5702, all of which are herein incorporated by reference. The Cre sequences may also be synthesized using plant-preferred codons. Such sequences (moCre) are described in WO 99/25840, herein incorporated by reference.

It is further recognized that chimeric recombinases can be used in the methods of the present invention. By "chimeric recombinase" is intended a recombinant fusion protein which is capable of catalyzing site-specific recombination between recombination sites that originate from different recombination systems. That is, if the non-identical recombination sites utilized in the present invention comprise FRT and loxP sites, a chimeric FLP/Cre recombinase or active variant thereof will be needed or both recombinases may be separately provided.

Methods for the production and use of such chimeric recombinases or active variant thereof are described in U.S. Pat. No. 6,262,341 and U.S. Pat. No. 6,541,231, herein incorporated by reference.

EXAMPLES

Example 1

Available MPSS (Massively Parallel Signature Sequencing) data for the Arabidopsis genome was searched for intergenic regions that could potentially contain modulator elements. This data is available at a public website (mpss.udel.edu). MPSS is a technique described by Solexa, Inc. of Hayward, Calif. MPSS and related technologies have been described in publications by Brenner et al. (Nature Biotechnol. 2000, 18: 630-634, and PNAS, 2000, 97:1665-1670).

The following criteria were used to survey the Arabidopsis genome for potential modulating element sequences. First, tandemly arranged genes that have relatively short intergenic regions were located. The expression pattern of the individual genes in the tandem pairs was determined using Arabidopsis genome annotation information (TIGR ver 3) and parsing program (Phyton ver 2.3) with some modifications for experimental purposes. The intergenic regions flanked by tandem pairs of genes with different expression patterns were considered further. Basal or core promoter regions that have a TATA Box and previously known cis-elements were disregarded. As a result of this bioinformatic analysis, a locus containing two hsc70 (heat shock) genes separated by 1.4 Kb of intergenic space in Arabidopsis chromosome 5 was found. This intergenic region was chosen for further analysis.

For analysis of modulating elements, particle bombardment was used to deliver test constructs into embryogenic tissue cultures of soybean. The test constructs were designed to determine the ability of putative modulating elements to block enhancer action on a core promoter. Therefore, the candidate element was cloned between 35S enhancers and core promoter. This 5' region was used to control expression of a firefly luciferase gene. A *Renilla lucierase* gene under control of the maize ubiquitin promoter served as an internal control. About 24 hours after bombardment, luciferase expression was determined for the construct with the candidate modulator and for the co-introduced ubiquitin construct.

Two candidate DNA regions, a 1.4 kb intergenic region (hsc14) and approximately 3 kb of a 5' upstream region (hsc5) of the hsc70 gene were subcloned as approximately 500 bp fragments into the assay vector. The elements were cloned into the assay vector in both forward and reverse orientation. The vectors were introduced into soybean embryogenic suspensions by particle bombardment and luciferase activity was determined after about 24 hours. Table 1 shows luciferase activity derived from the assay vectors. Some of the elements such as 5-II, 5-III and 14-IV substantially blocked expression from the 35S enhancers.

Three DNA fragments (hsc14-II, hsc5-III and hsc5-IV) were selected for further analysis. These fragments were dissected into approximately 100 bp sequences and cloned into the assay vector. Three of the approximately 100 bp fragments (5-III-5, 5-IV-1, and 5-IV-2) showed strong enhancer blocking activity (Table 2). Luciferase expression with the 5-III-5, 5-IV-1, and 5-IV-2 containing constructs was 20% to 30% of the expression exhibited in the control. Controls were the 35S enhancer and core promoter without any candidate sequences between them.

The impact of four of the putative modulator sequences (5-III-5, 5-IV-1, 5-IV-2, and 14-II-2) were then assessed in transgenic cell lines generated by stable transformation of embryogenic tissue cultures. To accomplish this, the assay construct was introduced with a selectable marker gene that confers resistance to hygromycin. The construct used for these experiments is shown below. Transgenic events were recovered eight weeks after bombardment and the luciferase activity in each event was analyzed (Table 3). The effect of the modulator on 35S enhancer activity was compared to luciferase activity from events harboring a 35S/luciferase control construct. Fragments 5-III-5 and 5-IV-2 appeared to substantially block expression from the 35S enhancers.

Construct used for analysis of modulator elements in stably transformed soybean tissue.

Nos 3'—LUC-F—35S Core—Candidate seq.—35S En—Nos 3'—Hyg—35SPro ←←

TABLE 1

First round screening of modulating and insulator elements
(Percentages are based on lucifease activity measured in LUX units)

| | Orientation | | | |
|---|---|---|---|---|
| | Forward Orientation | | Reverse Orientation | |
| SEQ ID | % of Control | SD | % of Control | SD |
| 5-I | 16.47 | 0.96 | 64.23 | 18.18 |
| 5-II | 5.77 | 2.43 | 34.29 | 7.10 |
| 5-III | 9.28 | 1.94 | 14.36 | 0.21 |
| 5-IV | 13.98 | 3.45 | 18.14 | 2.98 |
| 5-V | 42.33 | 11.97 | 71.13 | 3.46 |
| 5-VI | 49.36 | 53.97 | 54.35 | 20.64 |
| 14-I | 36.18 | 2.11 | 57.52 | 32.01 |
| 14-II | 23.39 | 7.09 | 61.23 | 28.41 |
| 14-III | 36.35 | 9.58 | 44.17 | 21.79 |
| 14-IV | 9.83 | 3.55 | 28.36 | 14.19 |

TABLE 2

Second round screening of modulating and insulator elements

| | Orientation | | | |
|---|---|---|---|---|
| | Forward Orientation | | Reverse Orientation | |
| SEQ ID | % of Control | SD | % of Control | SD |
| 5-III-1 | 33.74 | 5.36 | 35.78 | 6.35 |
| 5-III-3 | 50.06 | 7.93 | 67.10 | 19.80 |
| 5-III-4 | 31.03 | 9.26 | 41.87 | 4.68 |
| 5-III-5 | 26.53 | 5.05 | 33.92 | 5.76 |
| 5-IV-1 | 39.34 | 14.53 | 24.37 | 6.29 |
| 5-IV-2 | 23.01 | 5.54 | 43.80 | 11.66 |
| 5-IV-3 | 41.37 | 9.32 | 32.78 | 4.44 |
| 5-IV-4 | 61.09 | 17.19 | 47.90 | 22.02 |
| 5-IV-5 | 87.80 | 6.74 | 83.02 | 19.60 |
| 14-II-1 | 99.63 | 35.84 | 76.43 | 29.53 |
| 14-II-2 | 63.36 | 18.93 | 84.69 | 41.55 |
| 14-II-3 | 71.73 | 19.70 | 59.10 | 31.68 |
| 14-II-4 | 138.43 | 46.73 | 147.02 | 61.76 |
| 14-II-5 | 97.49 | 25.77 | 157.55 | 47.52 |

TABLE 3

Gene expression modulating and insulator activity of selected DNA fragments in stable transformation measured in LUX

| | | Control | 5-III-5 | 5-IV-1 | 5-IV-2 | 14-II-2 |
|---|---|---|---|---|---|---|
| Forward Orientation | Average | 12223.4 | 2081.75 | 3713.02 | 2799.51 | 3645.24 |
| | | | 17.03% | 30.38% | 22.90% | 29.82% |
| | Median | 4344.59 | 746.462 | 565.954 | 552.149 | 1015.64 |
| | | | 17.18% | 13.03% | 12.71% | 23.38% |
| Reverse Orientation | Average | 9718.42 | 4625.82 | 5819.41 | 3706.221 | 2977.134 |
| | | | 47.60% | 59.88% | 38.14% | 30.63% |
| | Median | 4546.53 | 1715.64 | 1361.15 | 1621.15 | 1400.59 |
| | | | 37.74% | 29.94% | 35.66% | 30.81% |

Example 2

The modulators identified in the present work block the ability of enhancer elements to activate a core promoter. It is know in the literature that enhancers for constitutive activation of one promoter in a transgene cassette can inadvertently activate other promoters that should provide tissue specific expression. For example, the 35S enhancers controlling the expression of a marker gene can activate the expression of a co-delivered tissue specific gene. See Yoo et al. (2005) Planta 221:523-530. Table 4 provides an example of this phenomenon in maize. Construct 1 in Table 4 contains a bar gene under the control of the 35S promoter and associated enhancers. This construct also contains a gus gene under the control of the oleosin promoter. Oleosin normally provides expression in certain seed tissue such as the scutellum. This construct was introduced into maize by agrobacterium-mediated transformation. Plants were recovered and gus expression was analyzed in leaf tissue. These plants had an average GUS expression of 284 pMole MU u. This demonstrates that the 35S enhancers in the construct produced un-wanted expression of the oleosin promoter in leaves. Similar observations were made with constructs 2 and 3 in Table 2. Unlike the 35S promoter, the ubiqutin promoter in construct 4 did not activate the oleosin promoter in leaves. Two constructs harboring a modulating element (AT-5-IV-2) between the oleosin/GUS gene and 35S/bar gene were introduced into maize (constructs 5 and 6). Transgenic events with these constructs had low levels of GUS expression, far lower than controls lacking the modulator element. These results show that the modulator can block unwanted activation of tissue specific promoters.

pinII—indicates potato proteinase inhibitor. See Ryan (1990) Ann. Rev. Phytopath. 28:425-449; Duan et al. (1996) Nature Biotechnology 14:494-498.

Ubi indicates a ubiquitin promoter. See Christensen et al. (1989) Plant Mol. Biol. 12:619-632 and Christensen et al. (1992) Plant Mol. Biol. 18:675-689).

BAR indicates Streptomyces hygroscopicus phosphinothricin acetyl transferase (bar) genes. Leemans et al., De Greef et al., Bio/Technology 7:61 (1989), describe the production of transgenic plants that express chimeric bar genes coding for phosphinothricin acetyl transferase activity; genes which confer resistance to herbicides such as L-phosphinothricin.

MoPAT indicates a modified pat gene (phosphinothricin acetyl transferase (PAT)) which gives resistance glufosinate).

ADH1 indicates an alcohol dehydrogenase (Adh) gene promoter (see, e.g., Millar (1996) Plant Mol. Biol. 31:897-904).

OLE indicates a oleosin promoter (WO 00/0028058).

NOS indicates the nopaline synthase (nos) promoter (M. W. Bevan et al., 1983; L. Herrera-Estrella et al., 1983, R T. Fraley et al., 1983, M. De Block et al., 1984; R Hain et al., 1985).

35S indicates the Cauliflower Mosaic Virus 35S promoter (J. Odell et al., 1985; D. W. Ow et al., 1986; D. M. Shah et al., 1986).

GUS indicates a beta-glucuronidase gene (see, e.g., Jefferson et al. 1987, EMBO J. 6:3901-3907)

Corn plants were transformed using Agrobacterium transformation. Six different expression cassettes were used (Table 4).

TABLE 4

| CASSETTE | AVG GUS Score in Leaf (pMole_MU_u) | Range of GUS Score |
|---|---|---|
| 1) NOS:GUSINT:OLE 0.9KB PRO// 35S:ADH1 INTRON:BAR:PINII | 284 (13 plants) | 0-795 |
| 2) NOS:GUSINT:OLE//35S:ADH1 INTRON:BAR:PINII | 1165 (2003 data) | N/A |
| 3) OLE 0.9KB PRO:GUSINT:NOS// 35S:ADH1 INTRON:BAR:PINII | 237 (2003 data) | N/A |
| 4) OLE 0.9KB PRO:GUSINT:NOS// UBI:UBI INTRON:MOPAT:35S TERM | 0 (2003 data) | N/A |
| 5) OLE:GUSINT:NOS//AT-5-IV-2// 35S:O':ADH1 INTRON:BAR:PINII | 31 (11 plants) | 18-40 |
| 6) NOS:GUSINT:OLE PRO// AT-5-IV-2// 35S:O':ADH1 INTRON:BAR:PINII | 79 (15 plants) | 0-220 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid comprising a gene expression modulating element operably linked to a heterologous polynucleotide of interest, wherein said gene expression modulating element is SEQ. ID NO. 4, and said gene modulating element influences the expression of the polynucleotide of interest.

2. An isolated nucleic acid fully complementary to the isolated nucleic acid of claim 1.

3. The isolated nucleic acid of claim 1 wherein said polynucleotide of interest comprises a 35S promoter.

4. The isolated nucleic acid of claim 1 wherein said polynucleotide of interest comprises an ubiquitin promoter.

5. A transformed plant cell comprising the nucleic acid of claim 1.

6. The plant cell of claim 5 wherein said plant cell is a corn, soybean, sorghum, sunflower, safflower, wheat, rice, alfalfa, or oil-seed *Brassica* cell.

7. A transgenic plant comprising the nucleic acid of claim 1.

8. A transgenic seed from the plant of claim 7, wherein the transgenic seed comprises said nucleic acid.

9. The transgenic plant of claim 7 wherein said plant is corn, soybean, sorghum, sunflower, safflower, wheat, rice, alfalfa, or oil-seed *Brassica*.

* * * * *